(12) United States Patent
Hattori et al.

(10) Patent No.: US 7,687,251 B2
(45) Date of Patent: *Mar. 30, 2010

(54) METHOD FOR PRODUCING CELL CULTURE SUBSTRATE AND APPARATUS FOR PRODUCING CELL CULTURE SUBSTRATE

(75) Inventors: Hideshi Hattori, Tokyo (JP); Hideyuki Miyake, Tokyo (JP); Hironori Kobayashi, Tokyo (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 421 days.

This patent is subject to a terminal disclaimer.

(21) Appl. No.: 10/594,174

(22) PCT Filed: Mar. 24, 2005

(86) PCT No.: PCT/JP2005/005337

§ 371 (c)(1),
(2), (4) Date: Sep. 26, 2006

(87) PCT Pub. No.: WO2005/093039

PCT Pub. Date: Oct. 6, 2005

(65) Prior Publication Data

US 2007/0141697 A1 Jun. 21, 2007

(30) Foreign Application Priority Data

Mar. 26, 2004 (JP) .............................. 2004-091653

(51) Int. Cl.
  C12N 11/02 (2006.01)
  C12N 11/14 (2006.01)
  C12N 11/08 (2006.01)
(52) U.S. Cl. ...................... 435/177; 435/176; 435/180; 977/703

(58) Field of Classification Search ................. 435/177, 435/176, 180; 977/703
See application file for complete search history.

(56) References Cited

U.S. PATENT DOCUMENTS 4,789,601 A  12/1988  Banes (Continued)

FOREIGN PATENT DOCUMENTS

| EP | 1 246 011 A2 | 10/2002 |
| JP | 2-211865 | 8/1990 |
| JP | 2-245181 | 9/1990 |

(Continued)

OTHER PUBLICATIONS

G. Sagvolden, et al; "Cell adhesion force microscopy", Proc. Natl. Acad. Sci. USA, vol. 96, pp. 471-476, Jan. 1999 Biophysics.

(Continued)

*Primary Examiner*—Karen Cochrane Carlson
*Assistant Examiner*—Rosanne Kosson
(74) *Attorney, Agent, or Firm*—Ladas & Parry LLP

(57) ABSTRACT

A method for producing a cell culture substrate to which cells adhere in a finely processed pattern while retaining the pattern for a long period of time to culture the cells and a production apparatus used in the production method. The method includes: forming a patterning substrate by forming: on a base material, a light shielding portion, and a cell adhesive layer having adhesion to a cell and containing a cell adhesive material which is decomposed or denatured by an action of a photocatalyst upon energy irradiation so as to cover the light shielding portion; an energy irradiating process of irradiating energy to the patterning substrate from the base material side to form a pattern; and a cell adhesion process of making the cell adhere to the cell adhesion portion in a cell culture medium containing the cell and a culture medium.

6 Claims, 3 Drawing Sheets

U.S. PATENT DOCUMENTS

| | | | |
|---|---|---|---|
| 5,096,941 | A | 3/1992 | Harnden |
| 5,284,766 | A | 2/1994 | Okano et al. |
| 5,470,739 | A * | 11/1995 | Akaike et al. ............... 435/402 |
| 5,512,131 | A | 4/1996 | Kumar et al. |
| 5,593,814 | A | 1/1997 | Matsuda et al. |
| 5,602,029 | A | 2/1997 | Miyamoto |
| 5,669,303 | A | 9/1997 | Maracas et al. |
| 5,721,131 | A | 2/1998 | Rudolph et al. |
| 5,725,788 | A | 3/1998 | Maracas et al. |
| 5,900,160 | A | 5/1999 | Whitesides et al. |
| 5,981,425 | A | 11/1999 | Taoda et al. |
| 6,294,313 | B1 | 9/2001 | Kobayashi et al. |
| 6,368,838 | B1 * | 4/2002 | Singhvi et al. ............. 435/177 |
| 2002/0095219 | A1 | 7/2002 | Nelles et al. |
| 2002/0182633 | A1 | 12/2002 | Chen et al. |
| 2003/0089259 | A1 | 5/2003 | Damme et al. |
| 2003/0219889 | A1 | 11/2003 | Sumaru et al. |
| 2004/0235167 | A1 | 11/2004 | Miyake et al. |
| 2005/0186674 | A1 | 8/2005 | Miyake et al. |
| 2005/0208656 | A1 | 9/2005 | Miyake et al. |
| 2005/0255594 | A1 | 11/2005 | Miyake et al. |
| 2005/0266319 | A1 | 12/2005 | Miyake et al. |
| 2005/0279730 | A1 | 12/2005 | Miyake et al. |
| 2006/0019390 | A1 | 1/2006 | Miyake et al. |
| 2006/0183219 | A1 | 8/2006 | Miyake et al. |

FOREIGN PATENT DOCUMENTS

| | | |
|---|---|---|
| JP | 3-7576 | 1/1991 |
| JP | 03-198771 | 8/1991 |
| JP | 04-4869 | 1/1992 |
| JP | 04-94679 | 3/1992 |
| JP | 04-126071 | 4/1992 |
| JP | 04-126074 | 4/1992 |
| JP | 5-176753 | 7/1993 |
| JP | 6-335381 | 12/1994 |
| JP | 07-075547 | 3/1995 |
| JP | 7-99962 | 4/1995 |
| JP | 07-099962 | 4/1995 |
| JP | 07-308186 | 11/1995 |
| JP | 08-009960 | 1/1996 |
| JP | 9-240125 | 9/1997 |
| JP | 10-12545 | 1/1998 |
| JP | 2002-184752 | 6/2002 |
| JP | 2002-253204 | 9/2002 |
| JP | 2002-274077 | 9/2002 |
| JP | 2002-355026 | 12/2002 |
| JP | 2002-355031 | 12/2002 |
| JP | 2002-542883 | 12/2002 |
| JP | 2003-9860 | 1/2003 |
| JP | 2003-38170 | 2/2003 |
| JP | 2003-039399 | 2/2003 |
| JP | 2003-228172 | 8/2003 |
| JP | 2003-295428 | 10/2003 |
| JP | 2003-339373 | 12/2003 |
| JP | 2004-51 | 1/2004 |
| JP | 2004-57019 | 2/2004 |
| JP | 2004-344025 | 12/2004 |
| WO | 98/51785 | 11/1998 |

OTHER PUBLICATIONS

B.J. Spargo, etl al; "Spatially controlled adhesion, spreading, and differentiation of endothelial cells on self-assembled molecular monolayers" Proc. Natl. Acad. Sci. USA, vol. 91, pp. 11070-11074, Nov. 1994, Cell Biology.

Dan V. Nicolau, et al; "Control of the neuronal cell attachment by functionality manipulation of diazo-naphtho-quinone/novolak photoresist surface", Biosensors & Bioelectronics vol. 11. No. 12, pp. 1237-1252, 1996.

Woon-Seok Yeo, et al; "Electroactive Monolayer Substrates that Selectively Release Adherent Cells", Chembiochem 2001, No. 7/8, pp. 590-593.

Kyung-Soon Cho, et al; "The Effect of Energy Irradiation on the Volum Resistivity Properties of Low Density Polyethylene Film", Conference Record of the 1998 IEEE International Symposium on Electrical Insulation, Arlington, Virginia, USA, Jun. 7-10, 1998, pp. 194-196.

W. Chris Wilson, Jr. et al; "Cell and Organ Printing 1: Protein and Cell Printers", The Anatomical Record, Part A 272A: 491-496(2003).

* cited by examiner

METHOD FOR PRODUCING CELL CULTURE SUBSTRATE AND APPARATUS FOR PRODUCING CELL CULTURE SUBSTRATE

This application is the U.S. national phase of International Application No. PCT/JP05/05337, filed on Mar. 24, 2005, which claims priority to Japanese Application No. 2004-091653, filed on Mar. 26, 2004.

TECHNICAL FIELD

The invention relates to a method for producing a cell culture substrate to which cells are made to adhere in a finely processed pattern and an apparatus for producing the cell culture substrate.

BACKGROUND ART

At present, cell cultures of various animals and plants are performed, and also new cell culture methods are in development. The technologies of the cell culture are utilized, such as to elucidate the biochemical phenomena and natures of cells and to produce useful substances. Furthermore, with cultured cells, an attempt to investigate the physiological activity and toxicity of artificially synthesized medicals is under way.

Some cells, particularly a lot of animal cells have the adhesion dependency of adhering to some materials and growing thereon, and cannot survive for a long period under a flotation condition out of organisms. For culturing cells having such adhesion dependency, a carrier to which cells can adhere is necessary, and in general, a plastic culture dish with uniformly applied cell adhesive proteins such as collagen, fibronectin and the like is used. It is known that these cell adhesive proteins act on cultured cells, make the cells adhere easily, and exert an influence on the form of cells.

On the other hand, there is a technology reported of adhering cultured cells only onto a small part on a base material and arranging them. By such a technology, it is made possible to apply cultured cells to artificial organs, biosensors, bioreactors and the like. As the method for arranging cultured cells, there is a method adopted in which a base material having a surface that forms a pattern different in easiness of adhesion to cells is used, cells are cultured on the surface of this base material and allowed to adhere only onto surfaces processed so that cells adhere, and thereby the cells are arranged.

For example, in the patent document 1, an electric charge-retaining medium on which an electrostatic pattern is formed is applied to culture cells for the purpose of proliferating nerve cells in a form of circuit, and the like. Furthermore, the patent document 2 tries to arrange cultured cells on a surface on which a cell adhesion-inhibiting or cell adhesive photosensitive hydrophilic polymer has been patterned by a photolithography method.

Furthermore, the patent document 3 discloses a cell culture base material on which a substance such as collagen affecting on the adhesion ratio and form of cells is patterned, and a method for producing this base material by a photolithography method. By culturing cells on such a base material, a larger amount of cells can be adhered on a surface on which collagen or the like is patterned, to realize patterning of cells.

However, depending on its application, there is the case where such patterning of a cell culture portion is required to be a finely processed patterning. When carrying out patterning by photolithography using a photosensitive material as mentioned above, a fine pattern can be obtained. However, the cell adhesive material must have photosensitivity and there is therefore the problem that the range of the choice of a cell adhesive material is much narrowed because it is difficult to chemically modify such as biogenic polymers to impart such photosensitivity to these polymers. Also, in a photographic method using a photoresist, it is necessary to use a developer and the like, which sometimes have an adverse influence on cell culture.

Moreover, a microcontact printing method is proposed from George M. Whitesides at Harvard University as a method of forming a fine pattern of a cell adhesive material (for example, Patent Document 4, Patent Document 5, Patent Document 6 and Patent Document 7). However, this method has the problem that it is difficult to industrially produce a cell culture substrate having a pattern of a cell adhesive material by using this method.

If the functional differentiation of cells and the functionalization of a cell aggregate by laminate coculturing with heterocells can be attained while retaining a cell pattern, this is of deep significance in the fields of cell tissue technologies. However, it is generally difficult to retain a cell pattern while culturing cells for a long time. This is because the protein secreted from culture cells is adsorbed gradually with time to the surface of a cell adhesion inhibiting portion, whereby the surface of the cell adhesion inhibiting portion resultantly has cell adhesive property.

Patent Document 1: Japanese Patent Application Laid-Open (JP-A) No. 2-245181
Patent Document 2: JP-A No. 3-7576
Patent Document 3: JP-A No. 5-176753
Patent Document 4: U.S. Pat. No. 5,512,131
Patent Document 5: U.S. Pat. No. 5,900,160
Patent Document 6: JP-A No. 9-240125
Patent Document 7: JP-A No. 10-12545

DISCLOSURE OF INVENTION

Problem to be Solved by the Invention

In view of this situation, it has been desired to provide a new method for producing a cell culture substrate to which cells adhere in a finely processed pattern while retaining the pattern for a long period of time to culture the cells and a production apparatus used in the production method.

Means for Solving the Problem

The present invention provides a method for producing a cell culture substrate comprising: a patterning substrate forming process of forming a patterning substrate by forming: on a base material, a light shielding portion, and a cell adhesive layer having adhesion to a cell and containing a cell adhesive material which is decomposed or denatured by an action of a photocatalyst upon energy irradiation so as to cover the light shielding portion; an energy irradiating process of irradiating energy to the patterning substrate from the base material side to form a pattern consisting of: a cell adhesion inhibiting portion in which the cell adhesive material is decomposed or denatured, and a cell adhesion portion which is other than the cell adhesion inhibiting portion; and a cell adhesion process of making a cell adhere to the cell adhesion portion in a cell culture medium containing the cell and a culture medium.

According to the present invention, the above-mentioned cell adhesion portion and cell adhesion inhibiting portion are formed by the above-mentioned energy irradiating process. Therefore, in the above-mentioned cell adhesion process, the cell is allowed to adhere only to the cell adhesion portion in the medium by, for example, dipping the cell adhesive layer in the cell culture medium and the cells can be cultured in a finely processed pattern. Also, in the present invention, the patterning substrate provided with the above-mentioned light shielding portion and cell adhesive layer is formed in the above-mentioned patterning substrate forming process. Therefore, by irradiating the energy to the entire surface of the patterning substrate in the energy irradiating process, only the region where the light shielding portion is not formed can also be made to be the cell adhesion inhibiting portion where the cell adhesive material is decomposed or denatured. Consequently, a finely processed pattern consisting of the cell adhesion portion and the cell adhesion inhibiting portion can be formed.

In the invention, the above-mentioned cell adhesive layer may be a photocatalyst-containing cell adhesive layer containing a photocatalyst and the above-mentioned cell adhesive material. In this case, when energy is irradiated in the energy irradiating process, the photocatalyst contained in the photocatalyst-containing cell adhesive layer itself is excited whereby the cell adhesive material can be decomposed and denatured. It is therefore unnecessary to separately form, for example, a layer containing the photocatalyst and it is thereby possible to produce the cell culture substrate in an efficient manner.

Also, in the invention, the above-mentioned patterning substrate forming process may be a process of forming a patterning substrate by forming a photocatalyst-containing layer containing at least a photocatalyst and the above-mentioned light shielding portion on the above-mentioned substrate, and forming the above-mentioned cell adhesive layer on the photocatalyst-containing layer. In this case, because the cell adhesive layer is formed on the photocatalyst-containing layer, there is a little possibility of the cell being brought into direct contact with the photocatalyst when the cell is adhered to the cell adhesion portion in the cell adhesion process. It is therefore possible to produce a cell culture substrate reduced in risk of the cell being affected by the influence of the photocatalyst with time.

Also, in the invention, energy may be irradiated to the above-mentioned cell adhesion inhibiting portion during the above-mentioned cell adhesion process. This makes it possible to further decrease the adhesion of the cell adhesion inhibiting portion to the cell by the action of the photocatalyst upon the energy irradiation and further prevent the cell from adhering to the cell adhesion inhibiting portion.

Further, in the invention, the cell pattern retaining process of retaining the pattern of the cell adhered to the cell adhesion portion by irradiating energy to the cell adhesion inhibiting portion from the base material side may be carried out after the cell adhesion process. This is because even when the cultured cell adheres to the cell adhesion inhibiting portion, the cell on the cell adhesion inhibiting portion can be removed by the action of the photocatalyst upon energy irradiation, so that the cells can be retained in a finely processed pattern.

The present invention further provides an apparatus for producing a cell culture substrate, characterized in that the apparatus comprising: a substrate support portion for supporting a substrate; a cell culture medium retaining portion which retains a cell culture medium containing the cell and a culture medium, and has a pH adjusting means for retaining the pH of the cell culture medium and a temperature control means for retaining temperature of the cell culture medium; and an energy irradiation portion for irradiating the substrate with the energy.

According to the present invention, the above-mentioned apparatus of producing a cell culture substrate comprises the above-mentioned cell culture medium retaining portion, substrate support portion and energy irradiation portion. Therefore, when the cell is cultured in a cell culture medium, a protein and a cell adhered to a region of the substrate other than the region where the cell is cultured can be removed by such as energy irradiation. This ensures the provision of an apparatus for producing a cell culture substrate which enables the production of a cell culture substrate on which the cells are cultured in a finely processed pattern.

EFFECT OF THE INVENTION

According to the present invention, a cell culture substrate can be produced on which cells are cultured in a finely processed pattern and the substrate can be made to have the ability of culturing cells for a long period of time while retaining the cell pattern in the cell culture medium.

DESCRIPTION OF REFERENCES

Figure 1A:
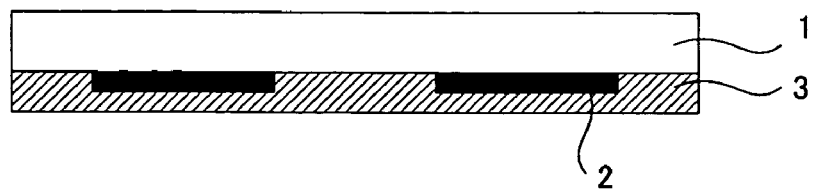
FIGS. 1A to 1D are a process drawing showing one example of a method for producing a cell culture substrate according to the present invention.
Figure 1B:
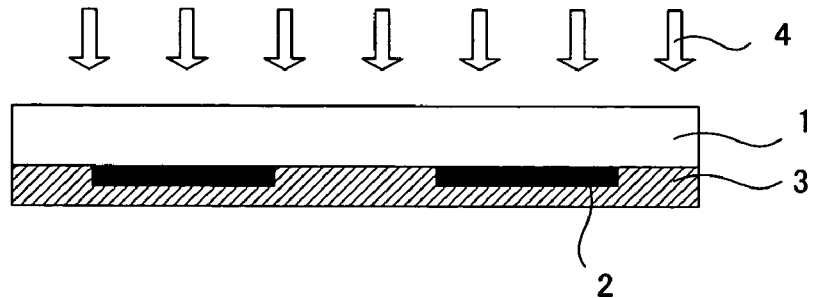

1: Base material
2: Cell culture region
3: Cell adhesion portion
4: Cell adhesion auxiliary portion
5: Photomask
6: Energy
7: Cell culture medium
8: Cell
9: Photocatalyst-containing layer
10: Cell adhesive layer
21: Substrate
22: Substrate support portion
23: Cell culture medium retaining portion
24: Energy irradiation portion

PREFERRED EMBODIMENTS OF THE INVENTION

The present invention relates to a method for producing a cell culture substrate to which cells adhere in a finely processed pattern and to an apparatus used to produce the cell culture substrate. The method and the apparatus will be explained separately.

A. Method for Producing a Cell Culture Substrate

First, a method of producing a cell culture substrate of the present invention will be explained. The method for producing a cell culture substrate of the invention comprising: a patterning substrate forming process of forming a patterning substrate by forming: on a base material, a light shielding portion, and a cell adhesive layer having adhesion to a cell and containing a cell adhesive material which is decomposed or denatured by the action of a photocatalyst upon energy irradiation so as to cover the light shielding portion; an energy irradiating process of irradiating energy to the patterning substrate from the base material side to form a pattern consisting of: a cell adhesion inhibiting portion in which the cell adhesive material is decomposed or denatured, and a cell adhesion portion which is other than the cell adhesion inhibiting portion; and a cell adhesion process of making the cell adhere to the cell adhesion portion in a cell culture medium containing the cell and a culture medium.

According to the present invention, the pattern consisting of the cell adhesion portion and the cell adhesion inhibiting portion is formed on the cell adhesive layer in the above-mentioned energy irradiating process. Therefore, in the above-mentioned cell adhesion process by, for example, dipping the cell adhesive layer in a cell culture medium, the cell can be easily adhered only to the cell adhesion portion and the cells can be cultured in an intended pattern in the cell culture medium. Also, in the present invention, energy is irradiated to the cell adhesion inhibiting portion from the above-mentioned base material side during or after the above-mentioned cell adhesion process, thereby making it possible, for example, to remove a protein and the cell adhered to the cell adhesion inhibiting portion to culture cells in a finely processed pattern.

Also, according to the present invention, the light shielding portion is formed between the cell culture layer and the base material in the above-mentioned patterning substrate forming process. Therefore, the cell adhesive material only in the region where the light shielding portion is not formed can be decomposed by irradiating energy to the entire surface from the base material side and it is therefore possible to form the cell adhesion portion and the cell adhesion inhibiting portion in a finely processed pattern with ease.

Here, in the present invention, there are two embodiments differing in the structure of the patterning substrate and in the energy irradiation method in the energy radiation process. Each embodiment will be explained in detail.

1. First Embodiment

First, a first embodiment of the method for producing a cell culture substrate according to the present invention will be explained. The method for producing a cell culture substrate according to the present invention comprises:

a patterning substrate forming process of forming a patterning substrate by forming: on a base martial, a light shielding portion, and a cell adhesive layer having adhesion to a cell and containing a cell adhesive material which is decomposed or denatured by the action of a photocatalyst upon energy irradiation so as to cover the light shielding portion;

an energy irradiating process of irradiating energy to the patterning substrate from the base material side to form a pattern consisting of: a cell adhesion inhibiting portion in which the cell adhesive material is decomposed or denatured, and a cell adhesion portion which is other than the cell adhesion inhibiting portion; and a cell adhesion process of making the cell adhere to the cell adhesion portion in a cell culture medium containing the cell and a culture medium, wherein the cell adhesive layer is made of a photocatalyst-containing cell adhesive material containing a photocatalyst and the cell adhesive material.

Figure 1C:
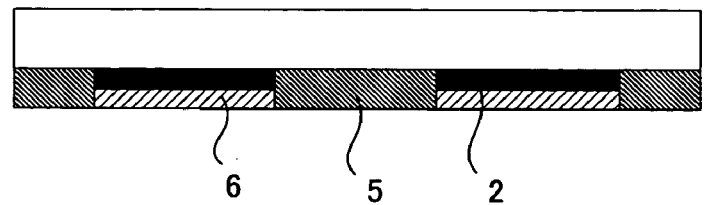
Figure 1D:
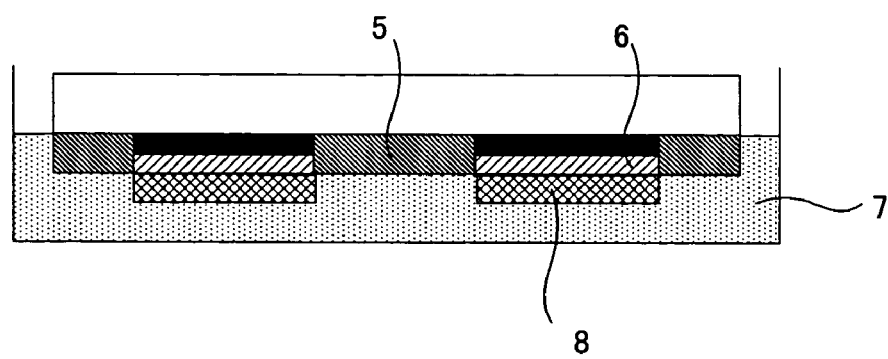

According to this embodiment, as shown in, for example, FIGS. 1A to 1D, first, a patterning substrate forming process is carried out in which a light shielding portion 2 is formed on a base material 1 and a photocatalyst-containing cell adhesive layer 3 containing a photocatalyst and a cell adhesive material is formed so as to cover the light shielding portion 2 to form a patterning substrate (FIG. 1A). In succession, an energy irradiating process is carried out in which an energy 4 is irradiated from the base material 1 side of the patterning substrate (FIG. 1B) to form a pattern consisting of: a cell adhesion inhibiting portion 5 reduced in adhesion to the cell because the cell adhesive material is decomposed or denatured by the action of the photocatalyst upon energy irradiation, and a cell adhesion portion 6 which is a region not irradiated with the energy 4 and therefore has high adhesion to the cell (FIG. 1C). Next, a cell adhesion process is carried out in which a cell 8 is made to adhere to the cell adhesion portion 6 in a cell culture medium 7 containing the cell and a culture medium (FIG. 1D), to produce a cell culture substrate in which the cell 8 is finely adhered only to the cell adhesion portion 6.

In this embodiment, since the photocatalyst-containing cell adhesive layer contains a photocatalyst and a cell adhesive material, the cell adhesive material can be decomposed or denatured by the action of the photocatalyst contained in the photocatalyst-containing cell adhesive layer itself when energy is irradiated in, for example, the energy irradiating process. It is therefore unnecessary to separately form a layer or the like containing the photocatalyst, thereby making it possible to improve the production efficiency of the cell culture substrate.

Hereinafter, each process of the method for producing a cell culture substrate in this embodiment will be explained.

(1) Patterning Substrate Forming Process

First, the patterning substrate forming process in this embodiment will be explained. The patterning substrate forming process in this embodiment is a process of forming a patterning substrate by forming: on a base martial, a light shielding portion, and a photocatalyst-containing cell adhesive layer containing a cell adhesive material which has adhesion to the cell and is decomposed or denatured by the action of a photocatalyst upon energy irradiation so as to cover the light shielding portion.

In this process, no particular limitation is imposed on the method of forming each member insofar as the light shielding portion and the photocatalyst-containing cell adhesive layer can be formed on the base material. For example, a process may be adopted in which the light shielding portion is formed on the base material and then a coating solution containing the photocatalyst and the cell adhesive material for forming the photocatalyst-containing cell adhesive layer is applied.

Hereinafter, each structure of the patterning substrate formed in this process will be explained.

(Photocatalyst-Containing Cell Adhesive Layer)

First, the photocatalyst-containing cell adhesive layer formed in this process will be explained. The photocatalyst-containing cell adhesive layer formed in this process is formed on the base material which will be explained later so as to cover the light shielding portion which will be explained later and contains the photocatalyst and the cell adhesive material.

In this process, any method may be used as the method of forming the photocatalyst-containing adhesion layer insofar as it can form such a layer. For example, a coating solution containing the photocatalyst and the cell adhesive material for forming the photocatalyst-containing cell adhesive layer may be applied by a wet method such as a spin coating method, a spray coating method, a dip coating method, a roll coating method, a bead coating method or a die coating method to form the photocatalyst-containing cell adhesive layer. The thickness of the photocatalyst-containing cell adhesive layer is appropriately selected according to the type of the cell culture patterning substrate and others. Usually, the thickness is about 0.01 µm to 1.0 µm, preferably about 0.1 µm to 0.3 µm.

Hereinafter, each materials used in the photocatalyst-containing cell adhesive layer will be explained.

a. Cell Adhesive Material

First, a cell adhesive material comprised in the photocatalyst-containing cell adhesive layer of the present process will be explained. The kind and the like of the cell adhesive material used in the present process is not particularly limited insofar as it has the cell adhesive property and can be decomposed or denatured by the action of a photocatalyst upon energy irradiation. Here, "having the cell adhesive property" means being good in the cell adhesion. For instance, when the cell adhesive property differs depending on the kind of cells, it means to be good in the adhesion with a target cell.

The cell adhesive material used in the present process has such cell adhesive property. Those losing the cell adhesive properties or those changed into ones having the cell adhesion-inhibiting properties of inhibiting adhesion to the cell, by being decomposed or denatured by the action of the photocatalyst upon energy irradiation, are used.

As such materials having the cell adhesive properties, there are two kinds, one being the material having the cell adhesive properties owing to physicochemical characteristics and the other being materials having the cell adhesive properties owing to biochemical characteristics.

As physicochemical factors that determine the cell adhesive properties of materials having the cell adhesive properties owing to the physicochemical characteristics, the surface free energy, the electrostatic interaction and the like can be cited. For instance, when the cell adhesive property is determined by the surface free energy of the material, if the material has the surface free energy in a predetermined range, the adhesive property between the cell and the material becomes good. If it deviates from the above-mentioned range the adhesive property between the cell and material is deteriorated. As such changes of the cell adhesive properties due to the surface free energy, experimental results shown in Data, for instance, CMC Publishing Co., Ltd. "Biomaterial no Saisentan", Yoshito Ikada (editor), p. 109, lower part are known. As materials having the cell adhesive properties owing to such a factor, for instance, hydrophilic polystyrene, poly(N-isopropyl acrylamide) and the like can be cited. When such a material is used, by the action of the photocatalyst upon energy irradiation, for instance, a functional group on a surface of the material is substituted, decomposed or the like to cause a change in the surface free energy, resulting in one that does not have the cell adhesive property or one that has the cell adhesion-inhibiting property.

When the adhesive property between cell and a material is determined owing to the electrostatic interaction or the like, for instance, the cell adhesive property is determined by an amount of positive electric charges and the like that the material has. As materials having the cell adhesive properties owing to such electrostatic interaction, basic polymers such as polylysine; basic compounds such as aminopropyltriethoxysilane, N-(2-aminoethyl)-3-aminopropyltrimethoxysilane; and condensates and the like including these can be cited. When such materials are used, by the action of the photocatalyst upon energy irradiation, the above-mentioned materials are decomposed or denatured. Thereby, for instance, an amount of positive electric charges present on a surface can be altered, resulting in one that does not have the cell adhesive property or one that has the cell adhesion-inhibiting property.

As materials having the cell adhesive properties owing to the biological characteristics, ones that are good in the adhesive properties with particular cells or ones that are good in the adhesive properties with many cells can be cited. Specifically, fibronectin, laminin, tenascin, vitronectin, RGD (arginine-glycine-asparagine acid) sequence containing peptide, YIGSR (tyrosine-isoleucine-glycine-serine-arginine) sequence containing peptide, collagen, atelocollagen, gelatin and the like can be cited. When such materials are used, by the action of the photocatalyst upon energy irradiation, for instance, a structure of the material is partially destroyed, or a principal chain is destroyed or the like, resulting in one that does not have the cell adhesive property or one that has the cell adhesion-inhibiting property.

Such a cell adhesive material, though it differs depending on the kind of the materials and the like, is comprised in the photocatalyst-containing cell adhesive layer normally in the range of 0.01% by weight to 95% by weight, and preferably in the range of 1% by weight to 10% by weight. Thereby, a region that contains the cell adhesive material can be made a region good in the cell adhesive property.

b. Photocatalyst

Next, a photocatalyst comprised in the photocatalyst-containing cell adhesive layer formed in the present process will be explained. The photocatalyst used in the present process is not particularly limited insofar as it can decompose or denature the cell adhesive material described above by the action of the photocatalyst upon energy irradiation.

Though the action mechanism of a photocatalyst typified by titanium oxide described below is not necessarily clear, it can be considered that a carrier generated by irradiation of light directly reacts with a nearby compound or, owing to an active oxygen species generated under the presence of oxygen, water, a chemical structure of an organic material is caused to be changed. In the present embodiment, it is considered that this carrier influences the function of the cell adhesive material described above in an energy irradiating process to be described later.

As the photocatalyst used in the present embodiment, specifically, for instance, titanium dioxide ($TiO_2$), zinc oxide (ZnO), tin oxide ($SnO_2$), strontium titanate ($SrTiO_3$), tungsten oxide ($WO_3$), bismuth oxide ($Bi_2O_3$) and iron oxide ($Fe_2O_3$) that are known as photo-semiconductors can be cited. These can be used singularly or in combination of at least two kinds.

In the present embodiment, in particular, titanium dioxide, owing to a large band gap, chemical stability, non-toxicity, and easy availability, can be preferably used. There are two types of titanium dioxide, anatase type and rutile type, and both can be used in the present embodiment; however, the anatase type titanium dioxide is more preferable. An excitation wavelength of the anatase type titanium dioxide is 380 nm or less.

As such anatase type titanium dioxide, for instance, an anatase titania sol of hydrochloric acid deflocculation type (trade name: STS-02, manufactured by ISHIHARA SANGYO KAISHA, LTD., average particle diameter: 7 nm, and trade name: ST-K01, manufactured by ISHIHARA SANGYO KAISHA, LTD.), an anatase titania sol of nitric acid deflocculation type (trade name: TA-15, manufactured by NISSAN CHEMICAL INDUSTRIES, LTD., average particle diameter: 12 nm) and the like can be cited.

The smaller is a particle diameter of the photocatalyst, the better, because a photocatalyst reaction is caused more effectively. It is preferable to use the photocatalyst with an average particle diameter of 50 nm or less, and one having an average particle diameter of 20 nm or less can be particularly preferably used.

Also, as the titanium oxide, a visible light-sensitive type may be used. The aforementioned visible light-sensitive type titanium oxide is those excited by the energy of visible light. As a method of developing a visible light-sensitive type, a method of nitriding titanium oxide is exemplified.

When titanium oxide ($TiO_2$) is nitrided, a new energy level is formed within the bandgap of titanium oxide ($TiO_2$), whereby the bandgap is narrowed. As a result, though the excitation wavelength of titanium oxide ($TiO_2$) is generally 380 nm, the resulting titanium oxide ($TiO_2$) can be excited by visible light having a wavelength longer than the above-mentioned excitation wavelength. This ensures that wavelengths of light in the visible light region by energy irradiation from various light sources can contribute to the excitation of titanium oxide ($TiO_2$) and it is therefore possible to highly sensitize titanium oxide.

Here, the nitriding treatment of titanium oxide so-called in this embodiment means: a treatment in which a part of oxygen sites of a titanium oxide ($TiO_2$) crystal is substituted with nitrogen atoms, a treatment in which a nitrogen atom is doped between lattices of a titanium oxide ($TiO_2$) crystal, or a treatment in which a nitrogen atom is disposed at the grain boundary between poly crystalline aggregates of a titanium oxide ($TiO_2$) crystal.

No particular limitation is imposed on the method of nitriding titanium oxide ($TiO_2$). Examples of the nitriding method include a method in which fine particles of crystalline titanium oxide is doped with nitrogen by heat treatment carried out at 700° C. in an ammonia atmosphere and the fine particles doped with nitrogen, an inorganic binder and a solvent are used to prepare a dispersion solution.

A content of the photocatalyst comprised in the photocatalyst-containing cell adhesive layer formed in the present embodiment can be set in the range of 5% by weight to 95% by weight, preferably of 10% by weight to 60% by weight, and more preferably of 20% by weight to 40% by weight. Thereby, a cell adhesive material of the photocatalyst-containing cell adhesive layer in a region where energy is irradiated in the energy irradiating process to be described later can be decomposed or denatured.

The photocatalyst used in the present embodiment is preferably low in the adhesiveness with the cell. Thereby, a region where the photocatalyst is exposed, owing to such as the decomposition of a cell adhesive material described above, can be used as a region low in the adhesiveness with the cell.

c. Others

In this embodiment, not only the cell adhesive material and the photocatalyst but also a binder etc. for improving strength, resistance etc. may be contained as needed in the photocatalyst-containing cell adhesive layer to be formed. In the present embodiment, particularly as the binder, a material that, at least after the energy irradiation, has the cell adhesion inhibiting property of inhibiting adhesion to the cell is preferably used. Thereby the adhesion between the cell and the cell adhesion inhibiting portion, which is a region irradiated with energy, in the energy irradiating process to be described later can thereby be reduced. As such a material, one that has the cell adhesion inhibiting property prior to the energy irradiation or one that obtains the cell adhesion inhibiting property by the action of the photocatalyst upon energy irradiation may be used.

In the present embodiment, a material that becomes to have the cell adhesion inhibiting property, particularly by the action of the photocatalyst upon energy irradiation, is preferably used as a binder. Thereby, in a region prior to the energy irradiation, the adhesiveness between the cell adhesive material and the cell is not inhibited, and only a region where energy is irradiated can be lowered in the adhesiveness with the cell.

As materials that can be used as such a binder, for instance, ones in which a principal skeleton has such a high bond energy that cannot be decomposed by the photo-excitation of the photocatalyst and an organic substituent can be decomposed by the action of the photocatalyst are preferably used. For instance, (1) organopolysiloxane that exhibits large strength by hydrolyzing or polycondensating chloro- or alkoxysilane or the like owing to a sol-gel reaction and the like, and (2) organopolysiloxane and the like in which reactive silicones excellent in the water repellency or oil repellency are crosslinked can be cited.

In the case of the (1), it is preferable to be organopolysiloxanes that are hydrolysis condensates or cohydrolysis condensates of at least one kind of silicon compounds expressed by a general formula:

(Here, Y denotes an alkyl group, fluoroalkyl group, vinyl group, amino group, phenyl group, epoxy group or organic group containing the above, and X denotes an alkoxyl group, acetyl group or halogen. "n" is an integer of 0 to 3). The number of carbons of the group expressed with Y is preferably in the range of 1 to 20, and the alkoxy group shown with X is preferably a methoxy group, ethoxy group, propoxy group or butoxy group.

As the reactive silicone according to the (2), compounds having a skeleton expressed by a general formula below can be cited.

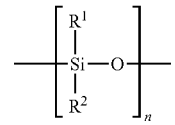

In the above-mentioned general formula, n denotes an integer of 2 or more, $R^1$ and $R^2$ each represents a substituted or nonsubstituted alkyl group, alkenyl group, aryl group or cyanoalkyl group having 1 to 20 carbons, and a vinyl, phenyl and halogenated phenyl occupy 40% or less by mole ratio to a total mole. Furthermore, one in which $R^1$ and $R^2$ is a methyl group is preferable because the surface energy is lowest, and a methyl group is preferably contained 60% or more by mole ratio. Still furthermore, a chain terminal or side chain has at least one or more reactive group such as a hydroxyl group in a molecular chain. When the material such as mentioned above is used, by the action of the photocatalyst upon energy irradiation, a surface of an energy-irradiated region can be made high in the hydrophilicity. Thereby, the adhesion with the cell is inhibited, and the region where energy is irradiated can be made into a region on which the cell does not adhere.

In the case of using the above-mentioned material as the cell adhesion-inhibiting material, the contact angle thereof with water is preferably in the range of 15° to 120°, more preferably in the range of 20° to 100° before the material is irradiated with energy. According to this, the cell adhesive property of the cell adhesive material can be rendered good.

In the case of irradiating this cell adhesion-inhibiting material with energy, it is preferred that the contact angle thereof with water becomes 10° or less. This range makes it possible to render the material having a high hydrophilicity and low cell adhesive property.

The contact angle with water referred to herein is a result obtained by using a contact angle measuring device (CA-Z model, manufactured by Kyowa Interface Science Co., Ltd.) to measure the contact angle of the material with water or a liquid having a contact angle equivalent to that of water (after 30 seconds from the time when droplets of the liquid are dropped down from its micro syringe), or a value obtained from a graph prepared from the result.

Together with the organopolysiloxanes, a stable organo silicium compound that does not cause a crosslinking reaction, such as dimethylpolysiloxanes, may be blended with a binder.

In the present embodiment, a decomposition substance or the like that causes such as a change in the wettability of a region where energy is irradiated, thereby lowers the adhesiveness with the cell or that aides such a change may be contained.

As such decomposition substances, for instance, surfactants or the like that are decomposed and the like, by the action of the photocatalyst upon energy irradiation, to be hydrophilic and the like to result in lowering the adhesiveness with the cell can be cited. Specifically, nonionic surfactants: hydrocarbon based such as respective series of NIKKOL BL, BC, BO, and BB manufactured by Nikko Chemicals Co., Ltd.; and silicone based such as ZONYL FSN and FSO manufactured by Du Pont Kabushiki Kaisha, Surflon S-141 and 145 manufactured by ASAHI GLASS CO., LTD., Megaface F-141 and 144 manufactured by DAINIPPON INK AND CHEMICALS, Inc., FTERGENT F-200 and F-251 manufactured by NEOS, UNIDYNE DS-401 and 402 manufactured by DAIKIN INDUSTRIES, Ltd., and Fluorad FC-170 and 176 manufactured by 3M can be cited. Cationic surfactants, anionic surfactants and amphoteric surfactants also can be used.

Other than the surfactants, oligomers and polymers such as polyvinyl alcohol, unsaturated polyester, acrylic resin, polyethylene, diallyl phthalate, ethylene propylene diene monomer, epoxy resin, phenol resin, polyurethane, melamine resin, polycarbonate, polyvinyl chloride, polyamide, polyimide, styrene-butadiene rubber, chloroprene rubber, polypropylene, polybutylene, polystyrene, polyvinyl acetate, nylon, polyester, polybutadiene, polybenzimidazole, polyacrylonitrile, epichlorohydrine, polysulfide, and polyisoprene can be cited.

In the present embodiment, such a binder can be preferably comprised in the photocatalyst-containing cell adhesive layer, in the range of 5% by weight to 95% by weight, more preferably 40% by weight to 90% by weight, and particularly preferably 60% by weight to 80% by weight.

(Light Shielding Portion)

Next, the light shielding portion formed in this process will be explained. The light shielding portion to be formed in this process is not limited in its shape and the like insofar as it is disposed between the above-mentioned photocatalyst-containing cell adhesive layer and the base material which will be explained later. For example, the light shielding portion is formed in the region which is to be formed as the cell adhesion portion in the energy irradiating process which will be explained later, specifically, in a region where the cell is cultured finally. In this embodiment, since the light shielding portion is formed between the base material and the photocatalyst-containing cell adhesive layer, no energy is irradiated to the photocatalyst-containing cell adhesive layer on the region where the light shielding portion is formed so that the cell adhesive material of this region is not decomposed even if energy is irradiated to the entire surface in the energy irradiating process which will be explained later.

No particular limitation is imposed on the method of forming the light shielding portion insofar as the energy irradiated in the energy irradiating process can be shielded. The light shielding portion may be formed by forming a metal (chromium or the like) thin film about 1000 to 2000 Å in thickness by, for example, a sputtering method or vacuum vapor deposition method and by carrying out patterning of this thin film. As the patterning method, an ordinary patterning method such as the sputtering can be used.

A method may be one by which a layer that contains light-shielding particles such as carbon particulates, metal oxides, inorganic pigments and organic pigments in a resin binder is formed in a pattern. As the resin binders that can be used, a polyimide resin, acrylic resin, epoxy resin, polyacrylamide, polyvinyl alcohol, gelatin, casein, cellulose and the like can be used singularly or in combination of two or more kinds, and furthermore a photosensitive resin and an O/W emulsion type resin composition such as emulsified reactive silicone can be used. A thickness of such the resinous light-light shielding portion can be set in the range of 0.5 μm to 10 μm. As a method for patterning such the resinous light-light shielding portion, methods such as a photolithography method and a printing method that are generally used can be used.

The light shielding portion may be formed on the side of the base material on which the photocatalyst-containing cell adhesive layer is to be formed or may be formed on the opposite surface.

When the light shielding portion is formed, a primer layer may be formed between the photocatalyst-containing cell adhesive layer and the light shielding portion. Although the action and function of this primer layer are not necessarily clarified, it is considered that when the primer layer is formed, it has the ability of preventing the diffusion of impurities, especially, residues produced when the light shielding portion is patterned or metal or metal ion impurities, which are intruded from an opening portion present in and between the light shielding portions and are a cause inhibiting the decomposition and denaturing of the cell adhesive material in the photocatalyst-containing cell adhesive layer wherein these decomposition and denaturing are effected by the action of the photocatalyst. Therefore, the formation of the primer layer ensures that the cell adhesive material can be decomposed and denatured at high sensitivity in the energy irradiating process which will be explained later, with the result that the cell adhesion portion and the cell adhesion inhibiting portion can be formed in a finely processed pattern.

Because the primer layer in this embodiment serves to prevent the influence of impurities existing not only in the light shielding portion but also in the opening portion formed between the light shielding portions on the action of the photocatalyst, the primer layer is preferably formed on the entire surface of the light shielding portion including the opening portion.

Any structure may be adopted for the primer layer in this embodiment insofar as the primer layer is formed so as to prevent the contact between the light shielding portion and the photocatalyst-containing cell adhesive layer.

A material that forms the primer layer, though not particularly limited, is preferably an inorganic material that is not likely to be decomposed by the action of the photocatalyst. Specifically, amorphous silica can be cited. When such amorphous silica is used, a precursor of the amorphous silica is preferably a silicon compound that is represented by a general formula, $SiX_4$, wherein X being halogen, methoxy group, ethoxy group, acetyl group or the like; silanol that is a hydrolysate thereof, or polysiloxane having an average molecular weight of 3000 or less.

A film thickness of the primer layer is preferably in the range of 0.001 μm to 1 μm and particularly preferably in the range of 0.001 μm to 0.1 μm.

(Base Material)

Next, the base material used for the patterning substrate formed in this process will be explained. Any material may be used as the base material used in this process without any particular limitation insofar as it enables the formation of the photocatalyst-containing cell adhesive layer and the light shielding portion and can transmit the energy irradiated in the energy irradiating process which will be described later. For example, inorganic materials such as glass and quartz and organic materials typified by plastics may be used as the base material. Also, the flexibility of the base material is properly selected according to such as the type and application of the cell culture substrate obtained finally.

(2) Energy Irradiating Process

Next, the energy irradiating process of this embodiment will be explained. The energy irradiating process in this embodiment is a process in which energy is irradiated to the patterning substrate from the base material side to form a pattern consisting of the cell adhesion inhibiting portion where the cell adhesive material is decomposed or denatured and the cell adhesion portion other than the above-mentioned cell adhesion inhibiting portion.

In this process, any method may be used as the energy irradiation method without any particular limitation as long as it enables the formation of the cell adhesion inhibiting portion where the cell adhesive material is decomposed or denatured by irradiating energy from the base material side of the patterning substrate so that the cell adhesion inhibiting portion is reduced in adhesion to the cell and the formation of the cell adhesion portion where the cell adhesive material remains because energy is not irradiated thereto so that the cell adhesion portion is highly adhesive to the cell. At this time, the cell adhesion inhibiting portion contains the photocatalyst and the decomposed or denatured products of the cell adhesive material consequentially.

In this embodiment, energy is usually irradiated to the entire surface from the base material side, and the region where the light shielding portion is not formed is the cell adhesion inhibiting portion and the region where the light shielding portion is formed is the cell adhesion portion. When the shape of the cell adhesion portion to be intended is wider than the shape of the light shielding portion, energy is irradiated through such as a photomask to decompose or denature the cell adhesive material corresponding to only the region to be intended, whereby the cell adhesion inhibiting portion can be formed.

Also, in this process, energy may be irradiated in the cell culture medium containing the cell and a culture medium which are used in the cell adhesion process which will be explained later. In this case, the cell adhesion process that will be explained later and the energy irradiating process can be carried out in the same apparatus or the like, and the production efficiency of the cell culture substrate can be improved accordingly. At this time, though the patterning substrate may be fully immersed in the cell culture medium to apply energy, it is preferable that only the photocatalyst-containing cell adhesive layer of the patterning substrate is brought into contact with the cell culture medium in this embodiment. This is because the transmission efficiency of the irradiated energy can be improved and therefore, the cell culture substrate can be produced efficiently. Here, the description that the photocatalyst-containing cell adhesive layer is brought into contact with the cell culture medium implies that not only the photocatalyst-containing cell adhesive layer is brought into contact with the cell culture medium but also the photocatalyst-containing cell adhesive layer is fully immersed in the cell culture medium.

The energy irradiation (exposure) mentioned in this embodiment is a concept that includes all energy ray irradiation that can decompose or denature the cell adhesive material by the action of the photocatalyst upon energy irradiation, and is not limited to light irradiation.

Normally, a wavelength of light used in such energy irradiation is set in the range of 400 nm or less, and preferably in the range of 380 nm or less. This is because, as mentioned above, the photocatalyst that is preferably used as a photocatalyst is titanium dioxide, and as energy that activates a photocatalyst action by the titanium dioxide, light having the above-mentioned wavelength is preferable.

When the aforementioned visible light-sensitive photocatalyst is used, light having a wavelength exceeding 400 nm may be used when the photocatalyst is irradiated with energy.

As a light source that can be used in such energy irradiation, a mercury lamp, metal halide lamp, xenon lamp, excimer lamp and other various kinds of light sources can be cited. Here, as mentioned above, when the base material is provided with the light shielding portion in the same pattern as the cell adhesion portion, the energy irradiation operation may be carried out by irradiating energy to the entire surface from the base material side.

Other than the method in which pattern irradiation is carried out via a photomask by using the above-mentioned light source, a method of carrying out drawing irradiation in a pattern by using laser such as excimer and YAG can be applied.

An amount of irradiated energy at the energy irradiation is an amount of irradiation necessary for decomposing or denaturing the cell adhesive material by the action of the photocatalyst.

At this time, by energy irradiating the photocatalyst-containing cell adhesive layer containing the photocatalyst while heating, the sensitivity can be raised; accordingly, it is preferable in that the cell adhesive material can be efficiently decomposed or denatured. Specifically, it is preferable to heat in the range of 30° C. to 80° C.

(3) Cell Adhesion Process

Next, the cell adhesion process in this embodiment will be explained. The cell adhesion process in this embodiment is a process in which the cell is made to adhere to the cell adhesion portion in the cell culture medium containing the cell and a culture medium.

Since the cell adhesion portion and the cell adhesion inhibiting portion are formed in the energy irradiating process, the cell is allowed to adhere only to the cell adhesive portion by, for example, dipping the cell adhesive layer in the cell culture medium containing the cell and its culture medium. In this embodiment, the cell is allowed to adhere to the cell adhesion portion in the cell culture medium, with the result that these cells can be cultured in a pattern to be intended.

The cells used in this cell culture medium may be cells of the tissues existing in a living body and cells derived from these tissues excluding non-adhesive cells such as a nerve tissue, liver, kidney, pancreas, blood, brain, cartilages and blood cells. Also, with regard to non-adhesive cells in general, there have been recently ideas as to technologies used to modify a cell membrane to adhere and fix these non-adhesive cells. If such technologies are used according to the need, these non-adhesive cells may also be used in this embodiment.

Here, each tissue such as those mentioned above is formed from cells having various functions and it is therefore necessary to select and use desired cells. In the case of, for example, the liver, it is formed from, besides hepatocyte, epithelial cells, endothelial cells, Kupffer's cells, fibroblast and fat-storing cells. In this case, because the adhesion to the cell adhesive materials differs depending on the type of cell, it is necessary to select the cell adhesive material used in the photocatalyst-containing cell adhesive layer and its percentage composition according to the type of cell.

The content of the cells is generally $10^4$/ml to $10^8$/ml and preferably $10^5$/ml to $10^7$/ml in the cell culture medium though it is selected appropriately according to the type of cell and the like. This is because cells of the above-mentioned content are allowed to adhere to the surface of the cell adhesion portion efficiently.

Also, the culture medium used in this process must be appropriately selected corresponding to the type of the cell. For example, the culture medium (culture medium) as described in "Soshikibaiyo no Gijyutsu, Dai San Han, Kiso", pp 3-5 (edited by The Japanese Tissue Culture Association) may be used. Also, commercially available culture mediums such as an Eagle's basal medium and Fisher's culture medium may be used.

Here, when this process is carried out, it is preferable that the temperature and pH of the cell culture medium are kept constant. This is to prevent because extinction of the cell.

Also, the cell adhesion inhibiting portion may be irradiated with energy continuously or intermittently while these cells are adhered to the cell adhesion portion in this process. This is because the cells and the like adhered to the surface of the cell adhesion inhibiting portion can be removed by the action of the photocatalyst contained in the photocatalyst-containing cell adhesive layer and these cells can be adhered only to the cell adhesion portion in a finely processed pattern. Here, any energy may be used as the energy to be irradiated without any particular limitation insofar as it can remove the cell and the like adhered to the surface of the cell adhesion inhibiting portion by the action of the photocatalyst. The same energy used in the energy irradiating process may be used. Also, when the shape of the cell adhesion portion is the same as that of the light shielding portion, cells on the cell adhesion inhibiting portion can be removed by irradiating energy to the entire surface from the base material side.

(4) Others

The method for producing a cell culture substrate according to this embodiment may comprise processes other than each of the above-mentioned process according to the need. For example, a cell pattern retaining process of irradiating energy to the cell adhesion inhibiting portion from the base material side to retain the pattern of the cells adhered to the cell adhesion portion may be carried out after the cell adhesion process. The reason is that even if the protein secreted from cells and these cells themselves are adhered to the cell adhesion inhibiting portion after the cell adhesion portion process, these cells can be removed by the action of the photocatalyst upon energy irradiation.

In the cell pattern retaining process, any method may be used as the energy irradiation method without any particular limitation insofar as cells and the like adhered to the surface of the cell adhesion portion can be removed by irradiating energy from the base material side. For example, this process may be carried out in the condition that the cell culture medium is in contact with the cell adhesive layer or may be carried out after the cell culture substrate to which cells are adhered is pulled up from the cell culture medium.

Here, the energy irradiation method in the cell pattern retaining process and the like may be the same as that in the energy irradiating process and therefore, the detailed explanations thereof are omitted.

2. Second Embodiment

Next, a second embodiment of the method for producing a cell culture substrate according to the present invention will be explained. The second embodiment of the method for producing a cell culture substrate according to the present invention comprises:

a patterning substrate forming process of forming a patterning substrate by forming: on a base material, a light shielding portion, and a cell adhesive layer having adhesion to a cell and containing a cell adhesive material which is decomposed or denatured by the action of a photocatalyst upon energy irradiation so as to cover the light shielding portion;

an energy irradiating process of irradiating energy to the patterning substrate from the base material side to form a pattern consisting of: a cell adhesion inhibiting portion in which the cell adhesive material is decomposed or denatured, and a cell adhesion portion which is other than the cell adhesion inhibiting portion; and a cell adhesion process of making the cell adhere to the cell adhesion portion in a cell culture medium containing the cell and a culture medium, wherein the patterning substrate forming process involves forming a photocatalyst-containing layer containing at least a photocatalyst and the light shielding portion on the base material and forming the cell adhesive layer on the photocatalyst-containing layer to make a patterning substrate.

Figure 2A:
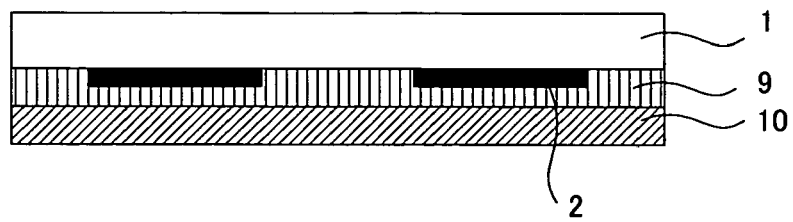
FIGS. 2A to 2D are a process drawing showing another example of a method for producing a cell culture substrate according to the present invention.
Figure 2B:
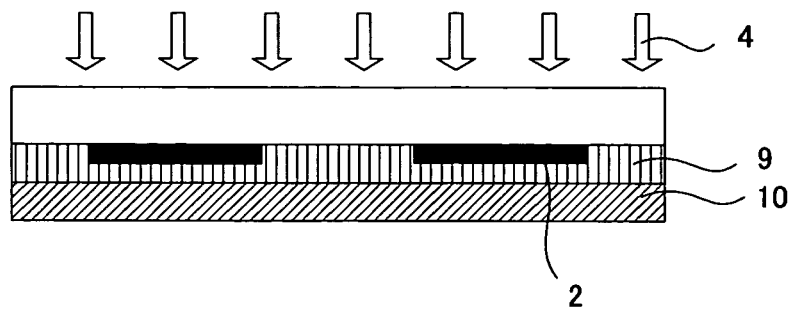
Figure 2C:
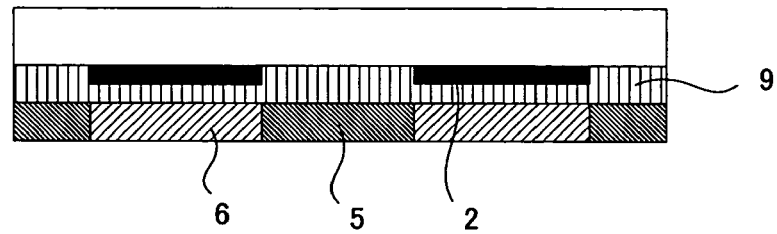
Figure 2D:
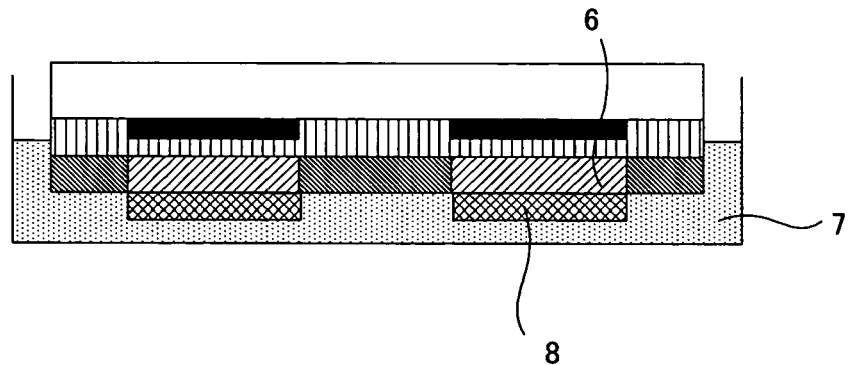

According to this embodiment, as shown in, for example, FIGS. 2A to 2D, first, a patterning substrate forming process is carried out in which a light shielding portion 2 is formed on a base material 1, a photocatalyst-containing layer 9 containing a photocatalyst is formed so as to cover the light shielding portion 2 and a cell adhesive layer 10 is formed on the photocatalyst-containing layer 9 to form a patterning substrate (FIG. 2A). In succession, an energy irradiating process is carried out in which an energy 4 is irradiated from the base material 1 side of the patterning substrate (FIG. 2B) to form a pattern consisting of a cell adhesion inhibiting portion 5 reduced in adhesion to the cell because the cell adhesive material is decomposed or denatured by the action of the photocatalyst contained in the photocatalyst-containing layer 9 and a cell adhesion portion 6 which is a region not irradiated with the energy 4 and therefore has high adhesion to the cell (FIG. 2C). Next, a cell adhesion process is carried out in which a cell 8 is made to adhere to the cell adhesion portion 6 in a cell culture medium 7 containing the cell and a culture medium (FIG. 2D), to produce a cell culture substrate in which the cell 8 is finely adhered only to the cell adhesion portion 6.

Figure 3:
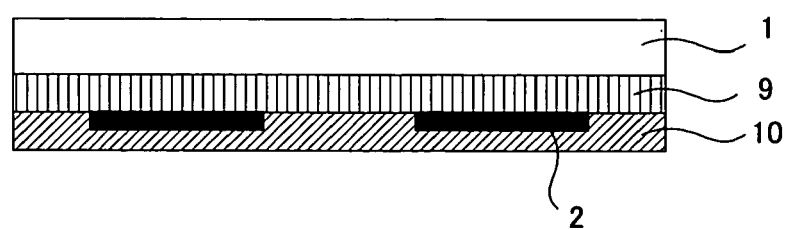
FIG. 3 is a schematic sectional view showing one example of a patterning substrate formed in a patterning substrate forming process in a method for producing a cell culture substrate according to the present invention.

In the patterning substrate forming process, for example, as shown in FIG. 3, the photocatalyst-containing layer 9 is formed on the base material 1, the light shielding portion 2 is formed on the photocatalyst-containing layer 9 and the cell adhesive layer 10 is formed so as to cover the light shielding portion 2.

In this embodiment, the cell adhesive layer containing the cell adhesive material and the photocatalyst-containing layer containing a photocatalyst are formed separately. Therefore, when energy is irradiated from the base material side in, for example, energy irradiating process, the photocatalyst in the photocatalyst-containing layer is excited to decompose or denature the cell adhesive material in the cell adhesive layer adjacent to the photocatalyst-containing layer. This embodiment has the advantage that the cell to be adhered in the cell adhesion process is eventually adhered to the surface of the cell adhesive layer, which decreases the possibility of the cells being brought into contact with the photocatalyst and therefore, the possibility of the cell being adversely affected by the photocatalyst with time is reduced. Moreover, in this embodiment, it is possible to use a cell adhesive material that cannot be directly mixed with the photocatalyst material or is very expensive. Hereinafter, the method for producing a cell culture substrate in this embodiment will be explained in each process.

(1) Patterning Substrate Forming Process

First, the patterning substrate forming process in this embodiment will be explained. The patterning substrate forming process in this embodiment is a process of forming a patterning substrate by forming: on a base material, a photocatalyst-containing layer containing at least a photocatalyst, the light shielding portion and a cell adhesive layer containing a cell adhesive material which has adhesion to the cell and is decomposed or denatured by the action of the photocatalyst upon energy irradiation.

In this process, no particular limitation is imposed on the structure of the patterning substrate or the like insofar as the patterning substrate can be formed. As mentioned above, the patterning substrate may be formed using a method in which the light shielding portion is formed on the base material, the photocatalyst-containing layer is formed so as to cover the light shielding portion and the cell adhesive layer is formed on the photocatalyst-containing layer, or a method in which the photocatalyst-containing layer is formed on the base material, the light shielding portion is formed on the photocatalyst-containing layer and the cell adhesive layer is formed so as to cover the light shielding portion. This is because in any of these cases, the influence of the action of the photocatalyst in the photocatalyst-containing layer can be prevented from extending to the region where the light shielding portion is formed when energy is irradiated from the base material side in the energy irradiating process which will be explained later, and this region may be made to be the cell adhesion portion. The light shielding portion may be formed on the surface of the base material on the side opposite to the surface on which the photocatalyst-containing layer and the cell adhesive layer are to be formed.

Each structure of the patterning substrate formed in this process will be explained. The base material, the light shielding portion, the primer layer and the like are the same as those in the aforementioned first embodiment and therefore, the detailed explanations of their structures are omitted.

(Cell Adhesive Layer)

First, the cell adhesive layer formed in this embodiment is described. The cell adhesive layer formed in this embodiment is a layer having at least a cell adhesive material having adhesion to the cell.

As the specific cell adhesive material, the same cell adhesive material used in the photocatalyst-containing cell adhesive layer described in the first embodiment can be used. Thus, its detailed description is omitted. Preferably, the cell adhesive layer formed in this embodiment also contains the material having cell adhesion-inhibiting property described in the photocatalyst-containing cell adhesive layer in the first embodiment. The cell adhesive property of the cell adhesion inhibiting portion, which is the energy-irradiated region formed in the energy irradiating process to be described later, can thereby be decreased.

Formation of the cell adhesive layer can be carried out by coating a cell adhesive layer forming coating solution containing the cell adhesive material by a general coating method. Since it can be carried out by the same method for forming the photocatalyst-containing cell adhesive layer in the first embodiment, its description is omitted.

Also, when the cell adhesive layer is formed after the photocatalyst-containing layer which will be explained later in this embodiment is formed, for example, the photocatalyst-containing layer may be dipped in the cell adhesive material-containing solution containing the cell adhesive material to form the cell adhesive layer on the photocatalyst-containing layer by an adsorption method. In this embodiment, the energy irradiating process which will be explained later may be carried out in a liquid, and also, the cell adhesion process is carried out in the cell culture medium. Therefore, even when, for example, a material less resistant to such as drying or oxygen is used as the cell adhesive material, the energy irradiating process is carried out in, for example, the cell adhesive material-containing solution or the cell culture medium and subsequently the cell adhesion process is carried out, whereby it is possible to prevent the cell adhesive material from being dried or denatured during the course of producing the cell culture substrate and to make the target cells adhere in pattern.

Examples of the cell adhesive material preferably used to form the cell adhesive layer in the cell adhesive material-containing solution include materials, such as proteins, which are deteriorated in their functions by drying. Examples of these materials include collagen, fibronectin and γ-globulin. Also, examples of the solvent used in the cell adhesive material-containing solution include water, alcohols, ethylene glycol, acids, buffer solutions and mediums.

The thickness of the cell adhesive layer is suitably selected depending on the type and the like of the cell culture patterning substrate. Usually, the thickness may be about 0.001 μm to 1.0 μm, preferably about 0.005 μm to 0.1 μm.

(Photocatalyst Containing Layer)

Now, the photocatalyst containing layer used in this step is described. The photocatalyst containing layer used in this step is not particularly limited insofar as it is a layer containing at least a photocatalyst. The photocatalyst containing layer may be a layer consisting of a photocatalyst only or may be a layer containing other component such as a binder.

The photocatalyst used in this embodiment can be the same as in the photocatalyst-containing cell adhesive layer in the first embodiment. The titanium oxide is also particularly preferably used in this embodiment.

The photocatalyst containing layer consisting of a photocatalyst only is advantageous in costs because the efficiency of decomposing or denaturing the cell adhesive material in the cell adhesive layer is improved to reduce the treatment time. On the other hand, use of the photocatalyst containing layer comprising a photocatalyst and a binder is advantageous in that the photocatalyst containing layer can be easily formed.

An example of the method for forming the photocatalyst containing layer made only of a photocatalyst may be a vacuum film-forming method such as sputtering, CVD or vacuum vapor deposition. The formation of the photocatalyst containing layer by the vacuum film-forming method makes it possible to render the layer a homogeneous photocatalyst containing layer made only of a photocatalyst. Thereby, the cell adhesive material can be decomposed or denatured homogeneously. At the same time, since the layer is made only of a photocatalyst, the cell adhesive material can be decomposed or denatured more effectively, as compared with the case of using a binder.

Another example of the method for forming the photocatalyst containing layer made only of a photocatalyst, is the following method: in the case that the photocatalyst is titanium dioxide, amorphous titania is formed on the base material, and then, calcinating so as to phase-change the titania to crystalline titania. The amorphous titania used in this case can be obtained, for example, by hydrolysis or dehydration condensation of an inorganic salt of titanium, such as titanium tetrachloride or titanium sulfate, or hydrolysis or dehydration condensation of an organic titanium compound, such as tetraethoxytitanium, tetraisopropoxytitanium, tetra-n-propoxytitanium, tetrabutoxytitanium or tetramethoxytitanium, in the presence of an acid. Next, the resultant is calcinated at 400° C. to 500° C. so as to be denatured to anatase type titania, and calcinated at 600° C. to 700° C. so as to be denatured to rutile type titania.

In the case of using a binder, the binder preferably having a high bonding energy, wherein its principal skeleton is not decomposed by photo-excitation of the photocatalyst. Examples of such a binder include the organopolysiloxanes described in the above-mentioned item "Cell Adhesive Layer".

In the case of using such an organopolysiloxane as the binder, the photocatalyst containing layer can be formed by dispersing a photocatalyst, the organopolysiloxane as the binder, and optional additives if needed into a solvent to prepare a coating solution, and coating this coating solution onto the base material. The used solvent is preferably an alcoholic based organic solvent such as ethanol or isopropanol. The coating can be performed by a known coating method such as spin coating, spray coating, dip coating, roll coating, bead coating or dye coating. When the coating solution contains an ultraviolet curable component as the binder, the photocatalyst containing layer can be formed by curing the coating solution through the irradiation of ultraviolet rays.

As the binder, an amorphous silica precursor can be used. This amorphous silica precursor is preferably a silicon compound represented by the general formula $SiX_4$, wherein X is halogen, methoxy group, ethoxy group, acetyl group or the like; a silanol which is a hydrolyzate thereof; or a polysiloxane having an average molecular weight of 3000 or less.

Specific examples thereof include such as tetraethoxysilane, tetraisopropoxysilane, tetra-n-propoxysilane, tetrabutoxysilane, and tetramethoxysilane. In this case, the photocatalyst containing layer can be formed by dispersing the amorphous silica precursor and particles of a photocatalyst homogeneously into a non-aqueous solvent, hydrolyzing with water content in the air to form a silanol onto a transparent base material, and then subjecting to dehydration polycondensation at room temperature. When the dehydration polycondensation of the silanol is performed at 100° C. or higher, the polymerization degree of the silanol increases so that the strength of the film surface can be improved. A single kind or two or more kinds of this binding agent may be used.

The content of the photocatalyst in the photocatalyst containing layer can be set in the range of 5% by weight to 60% by weight, preferably in the range of 20% by weight to 40% by weight. The thickness of the photocatalyst containing layer is preferably in the range of 0.05 μm to 10 μm.

Besides the above-mentioned photocatalyst and binder, the surfactant and so on used in the above-mentioned cell adhesive layer can be incorporated into the photocatalyst containing layer.

In the present embodiment, it is preferred that the surface of the photocatalyst containing layer is low in cell adhesive property by having, for example, high hydrophilicity on the surface for the following reason: this makes it possible, in the energy irradiating process to be described later, that when the cell adhesive layer is decomposed and the like to make the photocatalyst containing layer exposed, the exposed region is rendered a region low in cell adhesive property.

(2) Energy Irradiating Process

The energy irradiating process in this embodiment is a process of irradiating energy to the patterning substrate from the base material side to form a pattern consisting of the cell adhesion inhibiting portion where the cell adhesive material is decomposed or denatured and the cell adhesion portion which is other than the above-mentioned cell adhesive inhibiting portion.

In this process, any method may be used as the energy irradiation method without any particular limitation as long as it enables the formation of the cell adhesion inhibiting portion where the cell adhesive material is decomposed or denatured by irradiating energy from the base material side of the patterning substrate so that the cell adhesion inhibiting portion is reduced in adhesion to the cell, and the formation of the cell adhesion portion where the cell adhesive material remains because energy is not irradiated thereto so that the cell adhesion portion is highly adhesive to cells. At this time, when the cell adhesive material is decomposed by the action of the photocatalyst upon energy irradiation, the cell adhesive material is contained by a small amount or denatured products of the cell adhesive material is contained in the cell adhesion inhibiting portion consequentially. Alternatively, the cell adhesive layer is completely decomposed and removed to expose the photocatalyst-containing layer. Also, when the cell adhesive material is denatured by the action of the photocatalyst upon energy irradiation, its denatured products are contained in the cell adhesion inhibiting portion consequentially.

Also in this embodiment, energy is usually irradiated to the entire surface from the base material side, and the region where the light shielding portion is not formed is the cell adhesion inhibiting portion and the region where the light shielding portion is formed is the cell adhesion portion. When the shape of the cell adhesion portion to be intended is wider than the shape of the light shielding portion, energy is irradiated through such as a photomask to decompose or denature the cell adhesive material corresponding to only the region to be intended, whereby the cell adhesion inhibiting portion can be formed.

Also, in this process, as mentioned above, energy may be irradiated in the cell adhesive material-containing solution containing the cell adhesive material or the cell culture medium containing the cell and a culture medium which is used in the cell adhesion process which will be explained later. At this time, though the patterning substrate is fully immersed in the cell culture medium to apply energy, it is t preferable in this embodiment that the base material of the patterning substrate is not brought into contact with the cell culture medium. This is because the transmission efficiency of the irradiated energy can be improved and therefore, the cell culture substrate can be produced efficiently.

The type and irradiation method of energy to be irradiated in this process may be designed to be the same as those in the energy irradiating process of the aforementioned first embodiment and therefore, the detailed explanations are omitted here.

(3) Cell Adhesion Process

Next, the cell adhesion process in this embodiment will be explained. The cell adhesion process in this embodiment is a process in which the cell is adhered to the cell adhesion portion of the cell adhesive layer in the cell culture medium containing the cell and a culture medium.

Because the cell adhesion process in this embodiment may be made to be the same as that in the first embodiment, the detailed explanations are omitted here. In this embodiment, energy may be irradiated to the cell adhesion inhibiting portion when the cell is made to adhere to the cell adhesion portion.

(4) Others

Other than the above-mentioned each process, this embodiment may also comprise other processes according to the need. For example, a cell pattern retaining process of irradiating energy to the cell adhesion inhibiting portion from the base material side to retain the pattern of the cells adhered to the cell adhesion portion may be carried out after the cell adhesion process. The reason is that even if the protein and cells are adhered to the cell adhesion inhibiting portion after the cell adhesion portion process, these cells can be removed by the action of the photocatalyst upon energy irradiation.

The cell pattern retaining process may be designed to be the same as that in the first embodiment and therefore, its detailed explanations are omitted here.

B. Apparatus for Producing a Cell Culture Substrate

Next, the apparatus for producing a cell culture substrate according to the present invention will be explained. The apparatus for producing a cell culture substrate of the invention comprises: a substrate support portion that supports a substrate; a cell culture medium retaining portion which retains a cell culture medium containing the cell and a culture medium, and has a pH adjusting means for retaining the pH of the cell culture medium and a temperature control means for retaining the temperature of the cell culture medium; and an energy irradiation portion for irradiating the substrate with energy.

Figure 4:
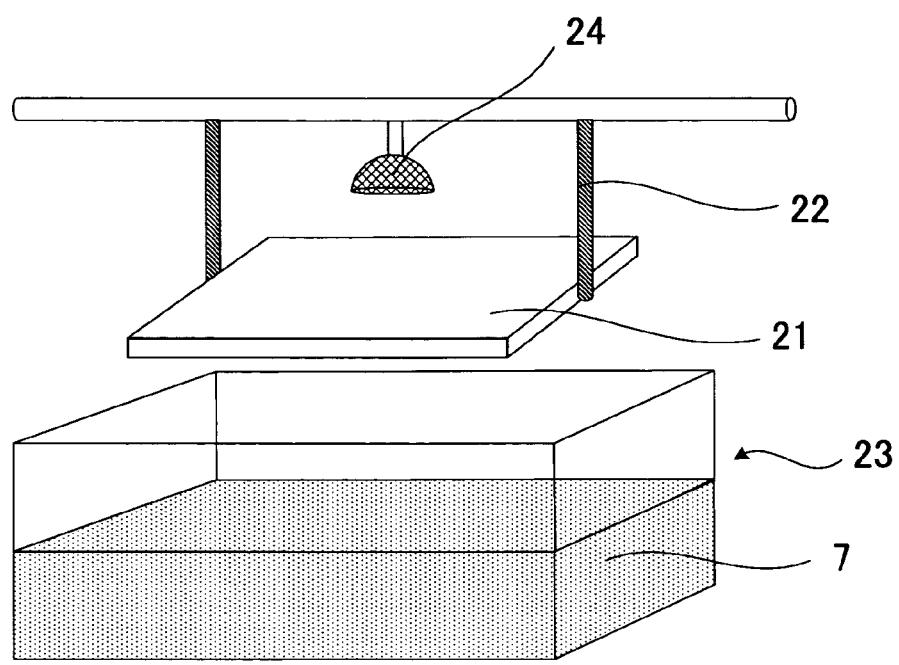
FIG. 4 is an explanatory view showing one example of an apparatus for producing a cell culture substrate according to the present invention.

The apparatus for producing a cell culture substrate according to the present invention, as shown in, for example, FIG. 4, is provided with a substrate support portion 22 that supports a substrate 21, a cell culture medium retaining portion 23 that retains a cell culture medium 7 and an energy irradiation portion 24 that irradiates the substrate with energy, wherein the cell culture medium retaining portion 23 is provided with a pH adjusting means (not shown in FIG. 4) that retains the pH of the cell culture medium 7 and a temperature control means (not shown in FIG. 4) that retains the temperature of the cell culture medium 7.

According the present invention, the apparatus for producing a cell culture substrate is provided with the cell culture medium retaining portion, the substrate support portion and the energy irradiation portion. Therefore, when cells are cultured in the cell culture medium by using, for example, a layer containing a photocatalyst, it is possible to remove protein and cells adhered to regions other than the substrate region by energy irradiation, thereby making it possible to produce a cell culture substrate on which cells are cultured in a finely processed pattern.

Here, the substrate used in the present invention is preferably a patterning substrate provided with a base material, a light shielding portion formed on the base material and a cell adhesive layer containing a cell adhesive material formed on the base material so as to cover the light shielding portion and contains a cell adhesive material which has adhesion to the cell and is decomposed or denatured by the action of the photocatalyst upon energy irradiation. This reason is as follows. Specifically, this structure ensures that the patterning substrate is supported by the substrate support portion and energy can be irradiated only to the region where the light shielding portion is not formed when the energy is irradiated from the base material side by the energy irradiation portion. It is thereby possible to form a pattern consisting of the cell adhesion inhibiting portion where the cell adhesive material in the cell adhesive layer is decomposed or denatured and the cell adhesion portion which is other than the cell adhesion inhibiting portion. In succession, this cell adhesive layer is dipped in the cell culture medium in the cell culture medium support portion to thereby make cells adhere only to the surface of the cell adhesion portion, whereby these cells can be cultured in the intended pattern. The energy irradiation may be carried out in the condition that the cell adhesive layer is dipped or not dipped in the cell culture medium.

In the present invention, the cell culture medium retaining portion and the energy irradiation portion are included in one apparatus. Therefore, energy can be irradiated to the cell adhesion inhibiting portion when or after cells are adhered in the cell culture medium. Even when proteins and cells are adhered on the cell adhesion inhibiting portion, these cells and the like can be removed by the action of the photocatalyst upon energy irradiation and it is therefore possible to make the cells adhere only onto the cell adhesion portion highly finely.

Hereinafter, each structure of the apparatus for producing a cell culture substrate according to the present invention will be explained.

1. Substrate Support Portion

First, the substrate support portion in the apparatus for producing a cell culture substrate according to the present invention will be explained. There is no particular limitation to the substrate support portion in the present invention insofar as it can support the substrate and the substrate support portion preferably has a structure enabling the height and position of the substrate to be controlled freely.

Also, this substrate support portion may be provided with a temperature control means that retains the temperature of the substrate. This is because the activity of the cell that adheres to the surface of the cell adhesion portion and the like can be retained and a high quality cell culture substrate can be therefore produced.

2. Cell Culture Medium Retaining Portion

Next, the cell culture medium retaining portion in the apparatus for producing a cell culture substrate according to the present invention will be explained. No particular limitation is imposed on the cell culture medium retaining portion in the present invention insofar as it retains the cell culture medium containing the cell and the culture medium and is provided with a pH adjusting means that retains the pH of the cell culture medium and a temperature control means that retains the temperature of the cell culture medium, and the apparatus may be provided such as with a stirring means according to the need.

In the present invention, the cell culture medium retaining portion that retains the cell culture medium is provided with the pH adjusting means and the temperature control means. Therefore, the pH and temperature of the cell culture medium can be kept constant and it is possible to prevent extinction of the cell and a deterioration in the activity of the cell. As such pH control means, one known to be used as a pH adjusting means in usual cell culture apparatuses may be used and therefore, its explanations are omitted here. Also, any temperature control means used as the temperature control means in usual cell culture apparatuses may be used as the temperature control means insofar as it can retain the temperature of the cell culture medium in the culture medium retaining portion. Therefore, the explanations of the temperature control means are omitted here.

3. Energy Irradiation Portion

Then, the energy irradiation portion in the apparatus for producing a cell culture substrate according to the present invention will be explained. Any irradiation material may be used as the material used in the energy irradiation portion in the present invention without any particular limitation insofar as it can apply energy to the substrate supported by the substrate support portion, by using, for example, a layer containing the photocatalyst to remove cells on the region irradiated with the energy to retain a cell pattern. The energy irradiation portion is preferably one capable of decomposing or denaturing the cell adhesive material contained in the cell adhesive layer of, particularly, the aforementioned patterning substrate by the action of the photocatalyst.

Any light source may be used as the light source that can be used such energy irradiation without any particular limitation insofar as it can activate the photocatalyst. Examples of the light source may include a mercury lamp, metal halide lamp, xenon lamp, excimer lamp and other various light sources. Also, light sources using such as an excimer laser or YAG laser may be used. This is because the use of these light sources makes it possible to excite the photocatalyst so that the cell adhesion portion can be formed.

4. Apparatus for Producing a Cell Culture Substrate

No particular limitation is imposed on the apparatus for producing a cell culture substrate according to the present invention insofar as it is provided with the above-mentioned substrate support portion, cell culture medium retaining portion and energy irradiation portion and the apparatus may have appropriate members according to the need. Also, the apparatus for producing a cell culture substrate according to the present invention is preferably used in, for example, the aforementioned "A. Process for producing a cell culture substrate".

The present invention is not limited to the aforementioned embodiments. These embodiments are examples and whatever has substantially the same structure and produces the same action effect as the technical idea described in the claim of the present invention is embraced by the technical scope of the present invention.

EXAMPLES

Examples of the present invention will be explained in more detail.

Example 1

Production of an Incubator with a Lamp

A commercially available incubator equipped with a pH adjusting function and a temperature control function was remodeled: specifically, a mercury lamp was installed on the ceiling part and a power source with a timer was set to the outside of the incubator. Also, a jig that could support the above-mentioned cell culture substrate on four corners and control the height of the substrate was set to the ceiling. Moreover, a cylinder containing 5% $CO_2$/95% Air and equipped with a regulator was connected to the incubator through a flow meter.

[Process of Forming a Patterning Substrate]

(Formation of a Photocatalyst-Containing Layer)

Mixed and stirred while heating at 100° C. for 20 minutes were 3 g of isopropyl alcohol, 0.4 g of organosilane TSL8114 (manufactured by GE Toshiba Silicones), and 1.5 g of a photocatalyst inorganic coating agent ST-KO1 (manufactured by ISHIHARA SANGYO KAISYA, LTD.).

A quarts glass substrate was formed which was 3 cm by 3 cm square and provided with a strip form light shielding layer having light shielding portions 80 μm in size and an opening portion 300 μm in size on the surface of a substrate by procedures producing a general chromium mask. The surface of this quarts glass substrate was coated with the photocatalyst coating solution by a spin coating method and this substrate was dried at 150° C. for 10 minutes to run hydrolysis and a polymerization condensation reaction to form, on the substrate, a photocatalyst-containing layer which had a film thickness of 0.2 μm with the photocatalyst firmly secured in organopolysiloxane.

(Formation of a Cell Adhesive Material-Containing Layer)

Mixed were 0.2 mg of fibronectin F-4759 (Sigma) and 200 ml of pure water and the aqueous solution thereof was dripped on the photocatalyst layer of the substrate provided with the photocatalyst-containing layer in advance with a ratio of 300 μl per 1 $cm^2$ of the substrate area. The substrate was allowed to stand at 4° C. for 24 hours. Moreover, the substrate was washed twice with PBS to obtain a patterning substrate provided with a photocatalyst-containing layer and a cell adhesive material-containing layer on the substrate. This substrate was transferred rapidly to the next process in the condition that it was dipped in PBS.

[Energy Irradiating Process]

PBS was poured into a Petri dish and the patterning substrate was supported by the jig in the incubator such that the surface to which fibronectin was adsorbed was made to face downward to dip the fibronectin adsorbed surface in PBS contained in the Petri dish. The substrate was exposed to ultraviolet ray from a mercury lamp disposed on the ceiling at an intensity of 6 $J/cm^2$ (measuring wavelength: 254 nm) to obtain a cell culture substrate having a cell adhesive surface patterned such that the unexposed portions had cell adhesive property and the exposed portions had cell adhesion inhibiting property.

[Cell Adhesive Process]

The procedures of an experiment made to culture cells derived from each tissue are described in detail in, for example, "Soshikibaiyo no Gijyutsu, Dai San Han, Kiso", edited by The Japanese Tissue Culture Association and published by Asakura Shoten. In this application of this case, the substrate was evaluated using a rat hepatocyte.

The liver excised from the rat was transferred to a Petri dish and cut by a knife into pieces 5 mm in size. 20 ml of a DMEM medium was added to these pieces, and the obtained medium was lightly suspended using a pipette and subjected to filtration using a cell filter. The obtained coarse dispersion cell float solution was centrifuged at 500 to 600 rpm for 90 seconds and the supernatant was removed by a suction means. Anew DMEM medium was added to the cell residue, which was then centrifuged again. This operation was repeated three times to obtain an almost uniform hepatocyte. 20 ml of a DMEM medium was added to the obtained hepatocyte, which was then suspended, to prepare a hepatocyte suspension solution.

Next, 900 ml of distilled water was added to 14.12 g of a Waymouth MB752/1 medium (containing L-glutamine and no $NaHCO_3$) (Gibco). 2.24 g of $NaHCO_3$, 10 ml of amphotericin B solution (ICN) and 10 ml of a penicillin streptomycin solution (Gibco) were added to the above-mentioned mixture, which was then stirred. The resulting mixture was adjusted to pH 7.4 to be a total amount of 1000 mL, which was then subjected to filtration using a 0.22 μm-membrane filter and sterilized to prepare a Waymouth MB752/1 medium solution.

The previously prepared hepatocyte suspension solution was suspended in the likewise prepared Waymouth MB752/1 medium solution and the suspension solution was disseminated on the aforementioned cell culture patterning substrate placed on the Petri dish. This substrate was allowed to stand under the condition of sterilization lamp-OFF, 37° C. and 5% $CO_2$ in the above-mentioned incubator for 24 hours to adhere the hepatocyte to the entire surface of the substrate.

This substrate was washed twice with PBS to remove non-adhesion cells and extinct cells. A new medium solution was added to a Petri dish and the cell-adhering surface of the above-mentioned substrate to which cells had been adhered was dipped in the medium solution such that the cell-adhering surface was made to face downward while supporting the substrate by the jig.

The medium solution was exchanged and the culturing of cells was continued until 48 hours passed to observe the condition of the cells by an optical microscope, to confirm that the cells were adhered along the cell adhesion portion of the cell culture patterning substrate.

Moreover, the medium solution was exchanged and culturing was continued for one week under the condition that the mercury lamp was applied for 5 minutes per 4 hours to confirm by the optical microscope observation that a cell aggregate was formed along the pattern of the substrate.

Example 2

Incubator with a Lamp

A commercially available incubator equipped with a pH adjusting function and a temperature control function was remodeled: specifically, a mercury lamp was installed on the floor part and a power source with a timer was set to the outside of the incubator. A tray supporting a Petri dish by using a metal wire about 3 mm in diameter was made and installed in place of the tray originally attached to the incubator. A cylinder containing 5% $CO_2$/95% Air and equipped with a regulator was connected to the incubator through a flow meter.

[Process of Forming a Patterning Substrate]

(Formation of a Photocatalyst-Containing Layer)

The same substrate that was used in Example 1 was used to carry out the same operation as in Example 1.

(Production of a Petri Dish with a Substrate)

A circle of about 2.5 cm in diameter was cut out of the center part of the bottom of a polystyrene Petri dish to apply the above-mentioned substrate having the photocatalyst layer to the cut part.

(Formation of a Cell Adhesive Material-Containing Layer)

The above-mentioned Petri dish was used to carry out the same operation as in Example 1, thereby forming a patterning substrate.

[Energy Irradiating Process]

The above-mentioned Petri dish (patterning substrate) with the cell adhesive material in which PBS was contained was set to the inside of the incubator set under the condition of 37° C. and 5% $CO_2$ while caring not to place the center of the Petri dish on the wire tray. The substrate was exposed to ultraviolet ray from a mercury lamp disposed on the floor at an intensity of 6 $J/cm^2$ (measuring wavelength: 254 nm) to obtain a cell culture substrate having a cell adhesive surface patterned such that the unexposed portions had cell adhesive property and the exposed portions had cell adhesion inhibitive property.

[Cell Adhesive Process]

The same experiment as in Example 1 was made, to also obtain the same result as in Example 1 in this example.

The invention claimed is:

1. A method for producing a patterned cell culture substrate comprising:
    forming on a base material, a light shielding element containing a material which can shield ultraviolet rays or visible light, and a cell adhesive layer containing a photocatalyst and a material to which cells adhere, wherein the light shielding element is sandwiched between the base material and the cell adhesive layer, and wherein the cell adhesive material is decomposed or denatured by action of the photocatalyst upon irradiation with ultraviolet rays or visible light;
    irradiating the patterning substrate from the base material side to form a pattern consisting of: a cell adhesion inhibiting portion in which the cell adhesive material is decomposed or denatured, and a cell adhesion portion which is other than the cell adhesion inhibiting portion;
    and attaching or adhering a cell to the cell adhesion portion, wherein the cell is in a cell culture.

2. The method for producing a cell culture substrate according to claim 1, wherein the cell adhesion inhibiting portion is further irradiated to further inhibit cell adhesion to the cell adhesion inhibiting portion.

3. The method for producing a cell culture substrate according to claim 1, wherein the pattern of the cells adhered to the substrate is retained by further irradiating the cell adhesion inhibiting portion to remove cells from the cell adhesion inhibiting portion after cells are attached or adhered to the cell adhesion portion.

4. A method for producing a patterned cell culture substrate comprising:
    forming on a base material, a light shielding element containing a material which can shield ultraviolet rays or visible light, a photocatalyst-containing layer, and a cell adhesive layer containing a material to which cells adhere and which is decomposed or denatured by action of the photocatalyst upon irradiation with ultraviolet rays or visible light, wherein the photocatalyst is contained in between the cell adhesive layer and the light shielding element, and wherein the light shielding element is sandwiched between the base material and the photocatalyst-containing layer which contacts the cell adhesive material;
    irradiating the patterning substrate from the base material side to form a pattern consisting of a cell adhesion inhibiting portion in which the cell adhesive material is decomposed or denatured, and a cell adhesion portion which is other than the cell adhesion inhibiting portion; and
    attaching or adhering a cell to the cell adhesion portion, wherein the cell is in a cell culture.

5. The method for producing a cell culture substrate according to claim 4, wherein the cell adhesion inhibiting portion is further irradiated to further inhibit cell adhesion to the cell adhesion inhibiting portion.

6. The method for producing a cell culture substrate according to claim 4, wherein the pattern of the cells adhered to the substrate is retained by further irradiating the cell adhesion inhibiting portion to remove cells from the cell adhesion inhibiting portion after cells are attached or adhered to the cell adhesion portion.

* * * * *